United States Patent
Ladd (12)

(10) Patent No.: US 6,656,149 B2
(45) Date of Patent: Dec. 2, 2003

(54) EXPANSIBLE MEDICAL SUCTION CANISTER

(76) Inventor: Leland L. Ladd, 7612 Eric St., Sylvania, OH (US) 43560

( * ) Notice: Subject to any disclaimer, the term of this patent is extended or adjusted under 35 U.S.C. 154(b) by 76 days.

(21) Appl. No.: 09/834,548

(22) Filed: Apr. 13, 2001

(65) Prior Publication Data

US 2001/0047158 A1 Nov. 29, 2001

Related U.S. Application Data

(60) Provisional application No. 60/196,946, filed on Apr. 13, 2000.

(51) Int. Cl.$^7$ .............................. A61M 1/06; A61M 1/00
(52) U.S. Cl. ........................ 604/73; 604/313; 604/316
(58) Field of Search .............................. 604/35, 37, 39, 604/40, 48, 73, 75, 76, 313, 316; 138/108, 114

(56) References Cited

U.S. PATENT DOCUMENTS

| | | | |
|---|---|---|---|
| 4,460,354 A | * 7/1984 | Weilbacher et al. ........ | 604/131 |
| 5,098,386 A | * 3/1992 | Smith ........................ | 604/152 |
| 5,197,322 A | * 3/1993 | Indravudh ................... | 604/141 |
| 5,342,329 A | * 8/1994 | Croquevielle ............... | 600/579 |

\* cited by examiner

*Primary Examiner*—Edward K. Look
*Assistant Examiner*—John K Fristoe, Jr.

(57) ABSTRACT

An expansible medical suction canister has an expansible chamber and a support. The chamber is expandable to an open position and compressible to a closed position. The chamber also has opposing first and second ends. The first and the second ends are spaced relatively farther apart in the open position than in the closed position. The support is connected between the opposing ends and moves with the opposing ends between the open and closed positions. The support also has a locked condition in the open position. The support may have a first element and a second element. The first and the second elements preferably move between open and closed positions with the opposing chamber ends. In one aspect, the first element may have a stop surface and the second element may include a leg with an end that abuts the stop surface in the open position, whereby compression of the canister to the closed position is resisted. In another aspect, the support may be a telescoping member with the first element including a detent and the detent engaging the second element. Further, the detent may be biased toward engagement with the second element.

20 Claims, 6 Drawing Sheets

EXPANSIBLE MEDICAL SUCTION CANISTER

CROSS-REFERENCES TO RELATED APPLICATIONS

This is a continuing non-provisional application of co-pending U.S. Provisional Patent Application Ser. No. 60/196,946, entitled Expansible Medical Suction Canister and filed on Apr. 13, 2000, by Leland L. Ladd and Gary A. Wagner, now abandoned, the disclosure of which is incorporated here by reference.

STATEMENT REGARDING FEDERALLY SPONSORED RESEARCH OR DEVELOPMENT

Not Applicable.

BACKGROUND OF THE INVENTION

The invention generally relates to medical care equipment and more particularly relates to fluids canisters and in particular suction canisters, which may be useful regarding irrigation suction fluids and other operatory fluids and which may also be useful in home and nursing home care.

It has become a self evident truth that competition reaches into virtually every segment of not only our national economy, but the world economy as well. The experts may discuss and argue without ending and without conclusion as to whatever may be the cause or reason of why the competitiveness of the economy is present. To some extent that is immaterial because it is here and must be accommodated or otherwise dealt with. At least one influence of the present competitiveness is an increasing demand on the available fluids of anyone in the market place. This includes non-discretionary as well as discretionary purchase decisions.

More specific to the invention, a focus has been drawn to the medical field and the expense of medical care. The medical services industry is an enormous industry. The resources, in terms of both people and funds, that are committed to providing medical care and services is incomprehensible to many. One effect of the competitive economy upon medical care is a drive to efficiency, which may be key phrased as doing more with less. Medical care is transitioning, if it has not already transitioned, to management and administration by professional administrators. This is no longer a profession that is driven by the professional medical care givers. Only one of a multitude of aspects of efficiency in medical care is the task of eliminating waste in physical facilities.

The professional managers and administrators are identifying and evaluating every factor and detail, large and small. Thus, materials and logistics control is important in medical services as in any industry. One of the little details that adds to a big allocation of resources is in the area of inventory, including the inventory of medical supplies and the disposal of consumed supplies and other medical waste, which is a hazardous waste disposal concern.

It is also self evident, then, that reducing the allocation of resources to the storage and handling of medical supplies and to the disposal of medical waste is important. After all, the more resources that can be freed from the "back room" tasks to the "front office" dispensing of medical care, the better. More specifically as to fluids canisters, the typical practice is to inventory a supply of canisters in a number of sizes, say one, two, and three liter, for example. Thus, the appropriate size canister may be selected for a given procedure. The physical storage space required for a proper supply of suction canisters may be reduced, freeing up allocated resources, if only one size canister is inventoried. The problem here is that a reduction in the variety of sizes that are inventoried may result in forcing the use of a larger than needed canister and associated increased disposal resources. A worse result is that a use of a number of small canisters may be imposed upon a medical procedure. Any medical procedure carries with it an inherent elevated stress or tension environment. Virtually any medical procedure also requires focused attention to various tasks. Thus, imposing an added requirement, and risk, of watching and changing small suction canisters is not justifiable.

Even the few, rudimentary factors noted above that are involved in the supply, use, and disposal of suction canisters demonstrate a desire for a one size canister that dose not compromise the dispensing of care or further burden its disposal. More particularly, these factors point to a desire for a suction canister that is small in storage of a supply inventory, provides maximum capacity during a medical procedure, and yet does not have added waste when disposed of. So far, an expandable and collapsible suction canister has not been practical if only because a canister that will not collapse under suction during use in a medical procedure also commonly resists compression for disposal.

BRIEF SUMMARY OF THE INVENTION

Accordingly, an expansible medical suction canister of the invention has an expansible chamber and a support. The chamber is expandable to an open position and compressible to a closed position. The chamber also has opposing first and second ends. The first and the second ends are spaced relatively farther apart in the open position than in the closed position. The support is connected between the opposing ends and moves with the opposing ends between the open and closed positions. The support also has a locked condition in the open position. The support may have a first element and a second element. The first and the second elements preferably move between open and closed positions with the opposing chamber ends. In one aspect, the first element may have a stop surface and the second element may include a leg with an end that abuts the stop surface in the open position, whereby compression of the canister to the closed position is resisted. In another aspect, the support may be a telescoping member with the first element including a detent and the detent engaging the second element. Further, the detent may be biased toward engagement with the second element.

These and other features, objects, and benefits of the invention will be recognized by one having ordinary skill in the art and by those who practice the invention, from this disclosure, including the specification, the claims, and the drawing figures.

DETAILED DESCRIPTION OF THE INVENTION

Figure 1:
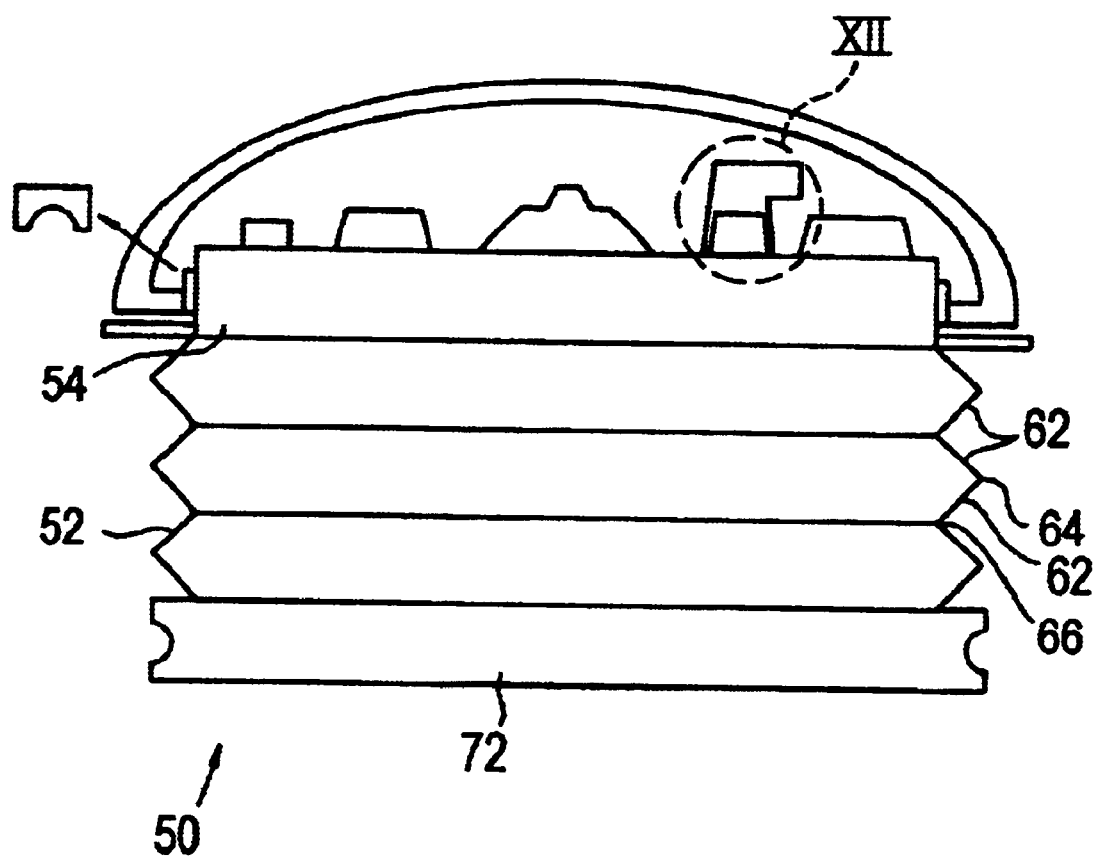
FIG. 1 is a side elevational schematic view of an expansible medical suction canister according to the invention, shown in a compressed condition.
Figure 2:
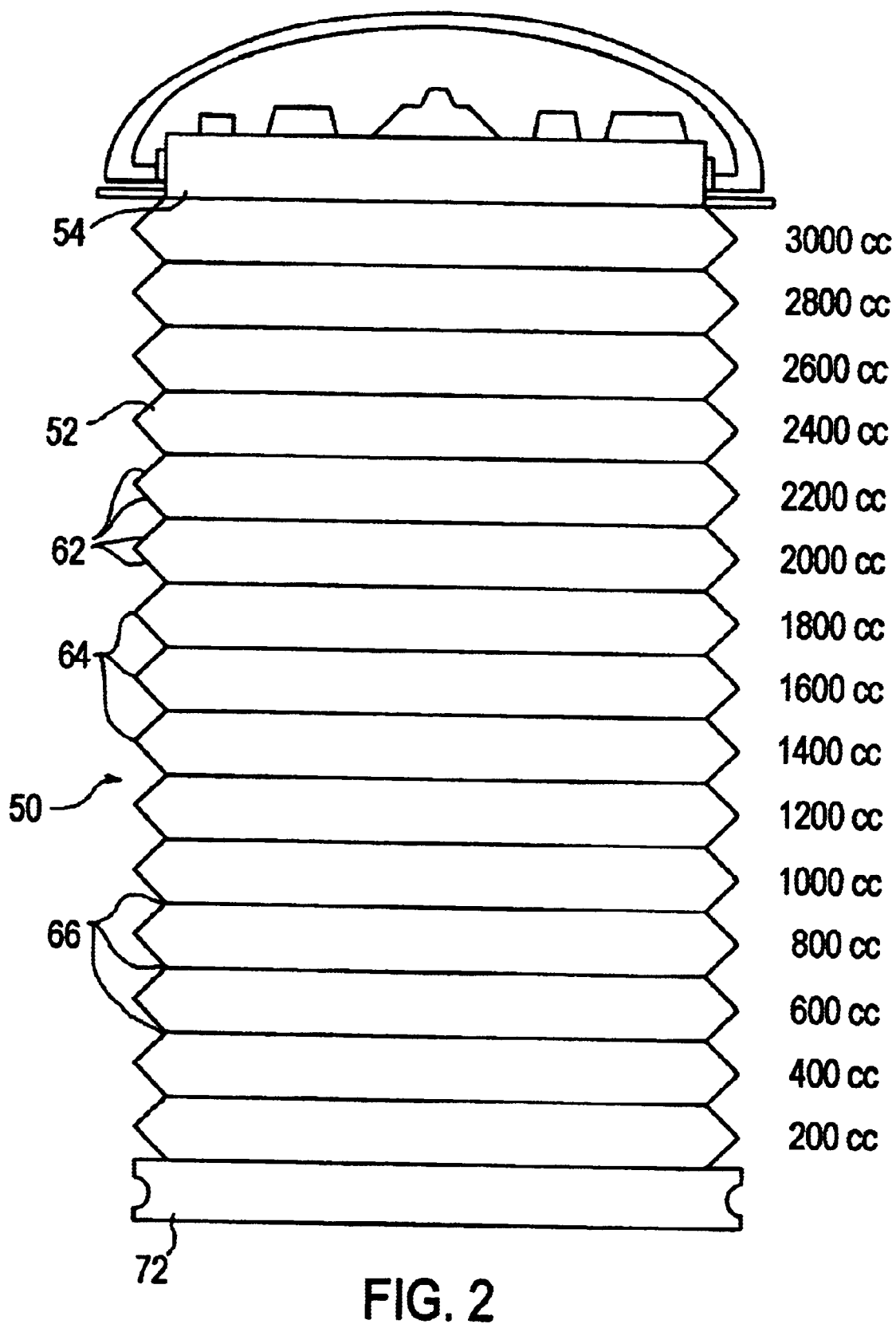
FIG. 2 is the view of FIG. 1, shown in an expanded condition.

A preferred embodiment of an expansible medical suction canister 50 according to the invention is generally shown in the drawing figures and discussed below. The expansible canister 50 may have a telescoping body 52 that defines a volume adjustable inner chamber. The canister 50 may also have a lid 54. The canister 50 may expand and compress between open and closed or expanded and compressed positions. While the body 52 may be provided with various telescoping or extensible configurations, as one having ordinary skill in the art will understand from this disclosure, the body 52 most preferably has a generally cylindrical side wall that is defined by an accordion or bellows configuration. Further, the body 52 is most preferably a one piece member that is constructed of a durable moldable material, including and not limited to, polyvinyl plastic.

More particularly, the side wall has a series of fan fold rings 62 that are hingedly interconnected at peaks 64 and valleys 66 by what is commonly known as a living hinge. If taken individually, each ring 62 defines a conic frustum. The side wall may be considered an array of alternating conic frustums that are hinged together. A bottom 72 may be integrally formed with the body 52 at one of two opposing ends, while a generally cylindrical ring is formed at the other end of the body and adapted to couple with the lid 54. The lid 54 and ring may be non-releasably snap-fit together or may be releasably screw-fit together, for example, as commonly known to one having ordinary skill in the art. Although, the canister may also be constructed without a lid per se. When provided as a disposable item of medical equipment, a user may prefer a non-releasable coupling of the lid 54 with the body 52. Clearly, the lid feature of the canister is quite variable and adaptable to a user's requirements.

Because the interior chamber is adjustable or expandable, provision must be made to lock or hold the chamber volume at a preselected size when a suction is drawn on the canister in use. One having ordinary skill in the art will understand that a volume adjustable canister will have an inherent tendency to collapse when a suction is applied to the interior chamber. By variation of the thickness of the rings and living hinges, and of the relative dimensions of the inner and outer diameters of the rings, compression and expansion force characteristics of the canister are varied. That is, the amount of suction that is required to collapse the canister may be adjusted and preset in manufacture of the canister, according to the specifications of the sidewall elements. An ability to sustain a suction of about thirty pounds per square inch (30 psi) is sufficient in most surgical use settings, for example.

Figure 3:
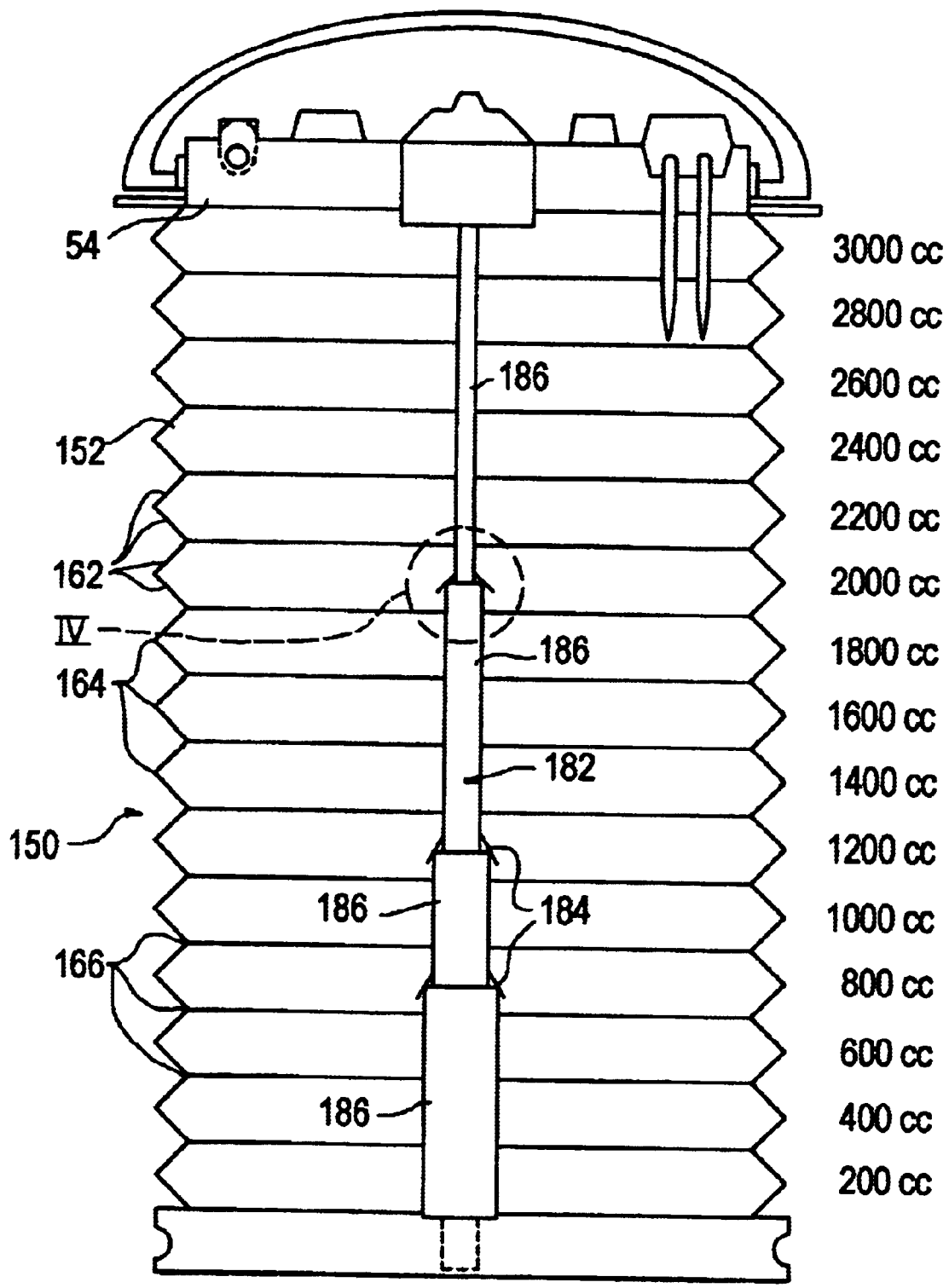
FIG. 3 is a centerline cross-sectional view thereof, showing a first alternative embodiment with a first locking support member.

In an alternative embodiment 150 (FIG. 3), the body 152 is constructed with rings 162 and hinges at peaks 164 and valleys 166, that are sized for relative ease of expansion and compression of the canister 150. Thus, a locking support 182 is provided to hold the canister 150 at a preselected volume expansion. The support 182 may be a telescoping member, which has a series of coaxial sliding elements or tubes 186 as is commonly known. Frangible legs 184 may be provided to hold the elements 186 at predetermined extended positions. The legs 184 hold the support 182 in a preselected extended position during use and may be forced to collapse when a user presses the canister down for disposal.

Figure 4:
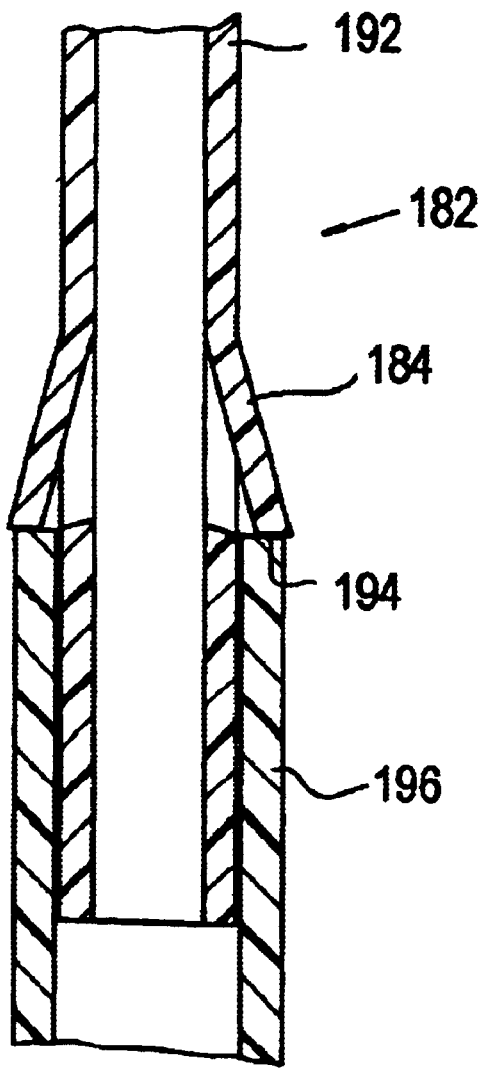
FIG. 4 is an enlarged fragmentary cross-sectional view of detail IV—IV of FIG. 3.

The legs 184 may be conveniently formed by punching, or the like, a portion of a side wall of an element 186. By constructing the element 186 of a length of plastic or metal tubing, for example, the legs 186 may be made to bias outward. Thus, the legs of an element 192 will spring out and abut an end 194 of an adjoining element 196 (FIG. 4), the end 194 defining a stop surface. Further, by selection of the material and thickness of a side wall of the element 192, a force required to collapse the legs 184 and the canister 150 may be predetermined as will be understood by one having ordinary skill in the art.

Figure 5:
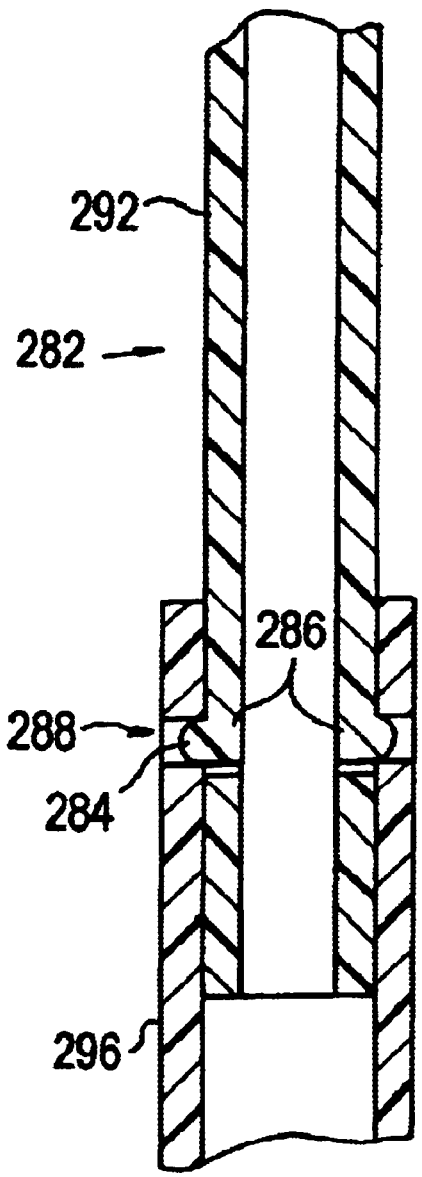
FIG. 5 is the view of FIG. 14, showing a first alternative.
Figure 6:
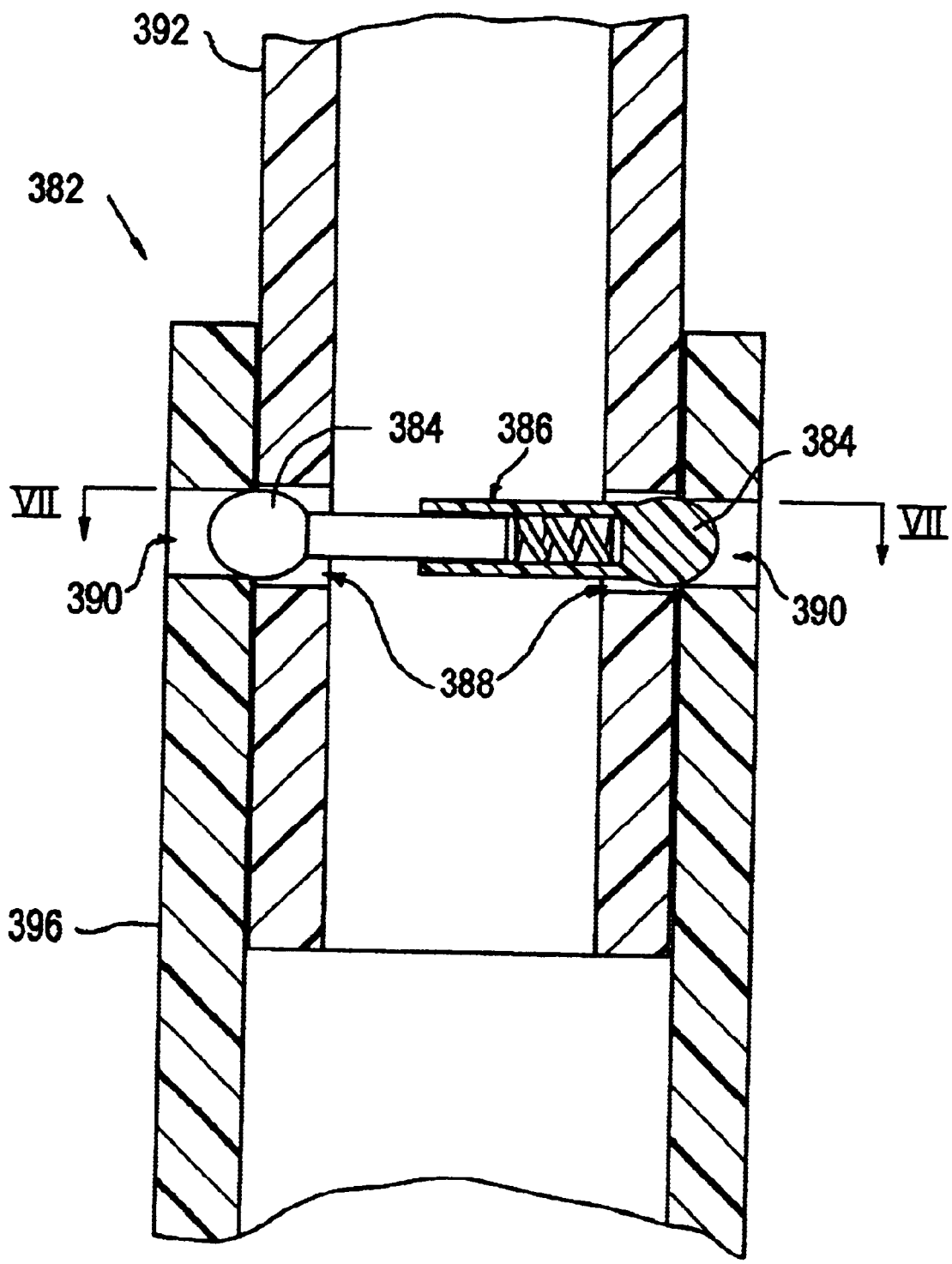
FIG. 6 is the view of FIG. 14, showing a second alternative.

In a first alternative 282 of the support 182, the legs 184 may be replaced with detents 284 on flexible tabs 286, or the like (FIG. 5). The detents 284 on one element 292 mate with cooperating detent receptacles, namely, apertures 288 of an adjoining element 296. In yet a second alternative 382 of the support 182, the legs 184 may be replaced with detents 384 on a spring rod 386, or the like (FIG. 6). The detents 384 slide freely through guides in the form of apertures 388 through one element 392 and mate in abutting engagement with cooperating detent receptacles or apertures 390 of an adjoining element 396. One having ordinary skill in the art will understand that any of the detents 284, the detents 384, the apertures 288 and the apertures 390 may be constructed with any of various cross-sectional geometries, or surface contours. Thus, a given detent geometry paired with a given aperture geometry will provide a particular strength of the locking support, either 282 or 382, relative to a force that may be applied to the canister and effect a compressing of the canister, including a suction that is drawn on the canister, for example. That is to say that a force that is required to compress the canister, or the resistance to that force, may be adjusted or pre-set by selection of the detent and the aperture geometries, and more particularly, specific pairings of the detent and the aperture geometries. It is a given, then, that the supports 282 and 382 may be constructed with a predetermined resistance to a canister compression force, and that the resistance may range from precluding compression of an open canister to virtually not resisting compression of an open canister.

Figure 7:
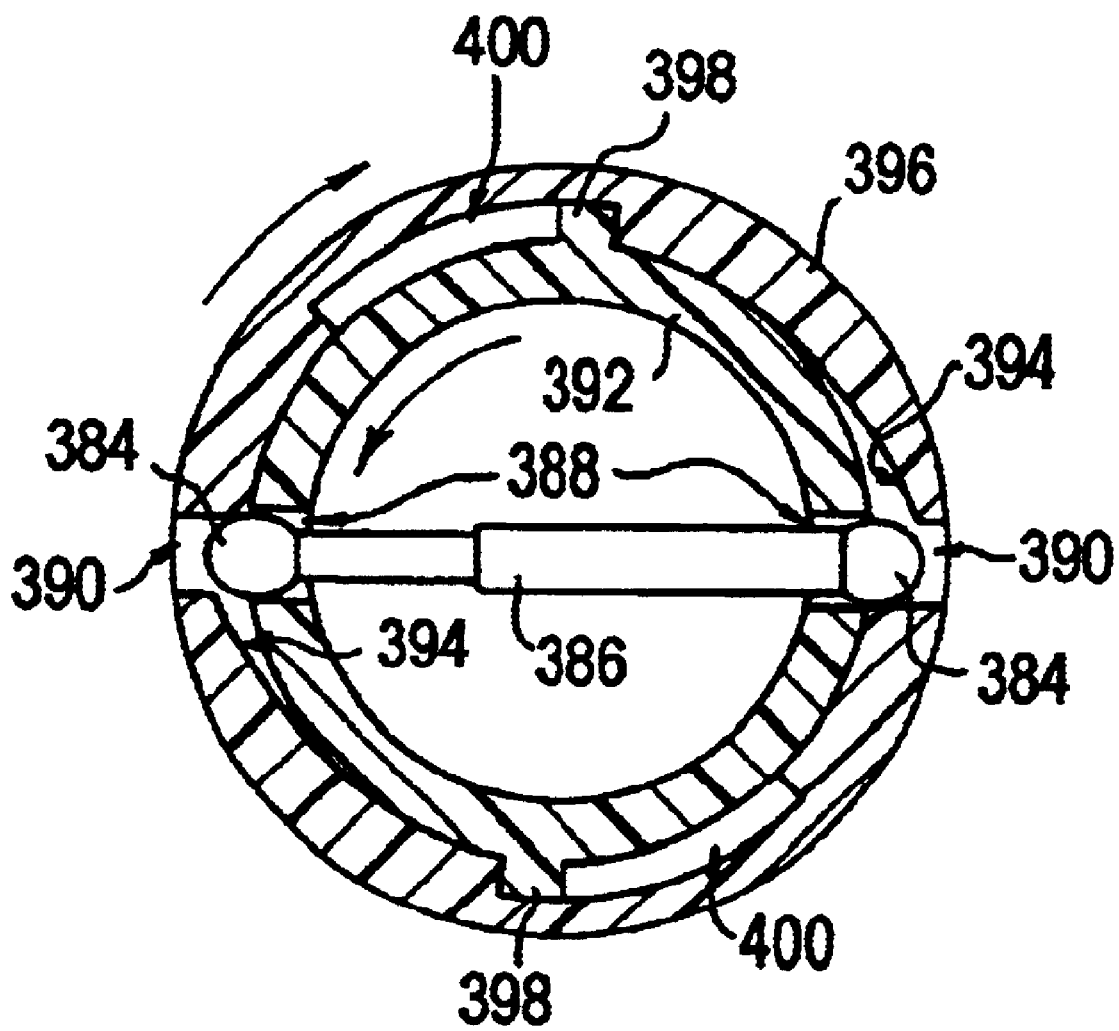
FIG. 7 is a cross-sectional view along line VII—VII of FIG. 6.

A release mechanism may further be provided with regard to either of the supports 282 and 382. While the release mechanism may be applied equally well to either of the supports 282 and 382, as will be understood from this disclosure by one having ordinary skill in the art, the release mechanism will be explained with reference to locking support 382 (FIG. 7). A rotary cam surface 394 may be formed in alignment with each aperture 390. Then by rotation of the elements 392 and 396 as shown by the arrows, the detents 384 are pressed inward and disengage the apertures 390. A rotation limit may also be employed by way of a tab 398 and slot 400.

One having ordinary skill in the art and those who practice the invention will understand from this disclosure that various modifications and improvements may be made without departing from the spirit of the disclosed inventive concept. One will also understand that various relational terms, including left, right, front, back, top, and bottom, for example, are used in the detailed description of the invention and in the claims only to convey relative positioning of various elements of the claimed invention. The scope of protection afforded is to be determined by the claims and by the breadth of interpretation allowed by law.

I claim:

1. An expansible medical suction canister comprising a body, the body having a top and an opposing bottom, the body defining an expansible interior chamber between the top and the bottom, the top having an access opening, the chamber being expandable to an open position and being compressible from the open position to a closed position; and a support connected between the top and the bottom, the support being adapted to releasably lock the chamber in the open position.

2. An expansible medical suction canister comprising:

a body, the body having a top and an opposing bottom, the body defining an expansible interior chamber between the top and the bottom, the top having an access opening, the chamber being expandable to an open position and being compressible from the open position to a closed position; and a support connected between the top and the bottom, the support being adapted to hold the chamber in the open position, the support being a telescoping member, the support having a first element and a second element, the first element including a detent, and the detent engaging the second element.

3. The expansible medical suction canister of claim 2 wherein the detent is a leg, wherein the second element has a stop surface, and the leg has an end that abuts the stop surface.

4. The expansible medical suction canister of claim 3 wherein the leg is frangible.

5. The expansible medical suction canister of claim 2 wherein the detent has a surface that engages the second element.

6. The expansible medical suction canister of claim 5 wherein the detent is biased toward engagement with the second element.

7. The expansible medical suction canister of claim 6 wherein the second element has a cooperating detent receptacle.

8. The expansible medical suction canister of claim 2 wherein the second element has a cooperating detent receptacle.

9. An expansible medical suction canister comprising:

a body, the body having opposing first and an second ends;

an expansible chamber in the body, the chamber being expandable to an open position and being compressible from the open position to a closed position, the opposing first and second ends being spaced apart in the closed position, the opposing first and second ends being spaced farther apart in the open position; and a support connected with the body, the support being adapted to releasably lock the canister in the open position.

10. The expansible medical suction canister of claim 9 wherein the support has a first element and a second element, wherein the first and the second elements move between open and closed positions with the canister, wherein the first element has a stop surface, wherein the second element includes a leg with an end that abuts the stop surface in the open position and compression of the canister to the closed position is resisted.

11. The expansible medical suction canister of claim 10 wherein the leg is frangible.

12. An expansible medical suction canister comprising:

a body, the body having opposing first and an second ends;

an expansible chamber in the body, the chamber being expandable to an open position and being compressible from the open position to a closed position, the opposing first and second ends being spaced apart in the closed position, the opposing first and second ends being spaced farther apart in the open position; and a support connected with the body, the support being adapted to hold the canister in the open position, the support being a telescoping member, the support having a first element and a second element, the first element including a detent, and the detent engaging the second element.

13. The expansible medical suction canister of claim 12 wherein the detent has a non-planar surface that engages the second element.

14. The expansible medical suction canister of claim 13 wherein the detent is biased toward engagement with the second element.

15. The expansible medical suction canister of claim 14 wherein the second element has a cooperating detent receptacle.

16. The expansible medical suction canister of claim 12 wherein the second element has a cooperating detent receptacle.

17. An expansible medical suction canister comprising:

an expansible chamber, the chamber being expandable to an open position and being compressible from the open position to a closed position, the chamber having a first end and an opposing second end, the first and the second ends being spaced relatively farther apart in the open position than in the closed position; and a support, the support being connected between the opposing ends, the support moving with the opposing ends between the open and closed positions, the support having a locked condition in the open position.

18. The expansible medical suction canister of claim 17 wherein the support has a first element and a second element, wherein the first and the second elements move between open and closed positions with the canister, wherein the first element has a stop surface, wherein the second element includes a leg with an end that abuts the stop surface in the open position and compression of the canister to the closed position is resisted.

19. An expansible medical suction canister comprising:

an expansible chamber, the chamber being expandable to an open position and being compressible from the open position to a closed position, the chamber having a first end and an opposing second end, the first and the second ends being spaced relatively farther apart in the open position than in the closed position; and a support, the support being connected between the opposing ends, the support moving with the opposing ends between the open and closed positions, the support having a locked condition in the open position, the support being a telescoping member, the support having a first element and a second element, the first element including a detent, and the detent engaging the second element.

20. The expansible medical suction canister of claim 19 wherein the detent is biased toward engagement with the second element.

* * * * *